United States Patent
Tanaka et al.

(10) Patent No.: US 12,122,918 B2
(45) Date of Patent: Oct. 22, 2024

(54) DRUG THAT REACTS WITH ACROLEIN, USE THEREOF AND NOVEL COMPOUND

(71) Applicant: RIKEN, Saitama (JP)

(72) Inventors: Katsunori Tanaka, Saitama (JP); Ambara Rachmat Pradipta, Saitama (JP)

(73) Assignee: RIKEN, Saitama (JP)

( * ) Notice: Subject to any disclaimer, the term of this patent is extended or adjusted under 35 U.S.C. 154(b) by 846 days.

(21) Appl. No.: 17/256,969

(22) PCT Filed: Jul. 5, 2019

(86) PCT No.: PCT/JP2019/026838
§ 371 (c)(1),
(2) Date: Mar. 1, 2021

(87) PCT Pub. No.: WO2020/009227
PCT Pub. Date: Jan. 9, 2020

(65) Prior Publication Data
US 2021/0179853 A1    Jun. 17, 2021

(30) Foreign Application Priority Data

Jul. 6, 2018 (JP) .................................. 2018-129372

(51) Int. Cl.
| | |
|---|---|
| *C09B 11/24* | (2006.01) |
| *C07C 15/00* | (2006.01) |
| *C07C 25/00* | (2006.01) |
| *C07C 35/00* | (2006.01) |
| *G01N 1/30* | (2006.01) |
| *G01N 33/52* | (2006.01) |

(52) U.S. Cl.
CPC .............. *C09B 11/24* (2013.01); *C07C 15/00* (2013.01); *C07C 25/00* (2013.01); *C07C 35/00* (2013.01); *G01N 1/30* (2013.01); *G01N 33/52* (2013.01); *G01N 2001/302* (2013.01)

(58) Field of Classification Search
CPC ......... C09B 11/24; C07C 15/00; C07C 25/00; C07C 35/00; G01N 1/30; G01N 33/52
See application file for complete search history.

(56) References Cited

PUBLICATIONS

Pradipta et al. ACS Sens. 2016, 1, 623-632 (Year: 2016).*
Supplementary—Pradipta et al. 2016 S1-S18 (Year: 2016).*
Kagakudojin 2016, vol. 71, No. 8, pp. 38-42.
Pradipta, A. R. et al., Unexplored Chemical Reactions of Endogenous Acrolein: Detection, Toxicity, and Biological Roles, Biofunctional Synthetic Chemistry Laboratory, RIKEN: 2-1 Hirosawa, Wako, Saitama 351-0198, Japan, Yakugaku Zasshi 137(3) pp. 301-306, 2017.
Pradipta, A. R et al., Uncatalyzed Click Reaction between Phenyl Azides and Acrolein: 4-Formyl-1,2,3-Triazolines as "Clicked" Markers for Visualizations of Extracellular Acrolein Released from Oxidatively Stressed Cells, ACS Sensors, 2016.04.12, vol. 1, pp. 623-632.
English translation of International preliminary report on patentability of PCT/JP2019/026838, mailed Jan. 12, 2021, 6 pages.
International Search Report for PCT/JP2019/026838, mailed Oct. 1, 2019, 2 pages.

* cited by examiner

*Primary Examiner* — Kortney L. Klinkel
*Assistant Examiner* — Richard Grant Peckham
(74) *Attorney, Agent, or Firm* — Casimir Jones, S.C.; Robert A. Goetz (57) ABSTRACT

Provided are, for example, (i) a drug that reacts with acrolein and (ii) a use thereof. A drug that reacts with acrolein in accordance with an embodiment of the present invention contains a compound having a chemical structure represented by Formula (1):

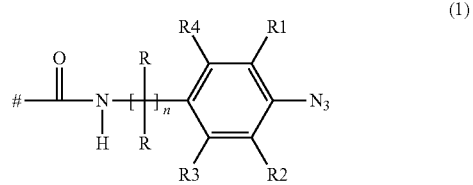

(1)

10 Claims, 3 Drawing Sheets

IDC: Invasive Ductal Carcinoma, DCIS: Ductal Carcinoma In Situ, Blue: Nuclei (DAPI).

FIG. 3

DRUG THAT REACTS WITH ACROLEIN, USE THEREOF AND NOVEL COMPOUND

TECHNICAL FIELD

The present invention relates to, for example, (i) a drug that reacts with acrolein and contains a compound having a specific structure and (ii) a use thereof.

BACKGROUND ART

Acrolein ($CH_2$=CHCHO) is the smallest-sized unsaturated aldehyde molecule and is a very highly reactive molecule. Acrolein is known to be generated during burning of an organic matter. In addition, for example, in oxidative stress-related diseases such as cancer, Alzheimer's disease, and cerebral infarction, acrolein is considered to be generated in vivo in the form of a lipid metabolite and/or a polyamine metabolite.

Furthermore, a recent study has made it clear that acrolein is more toxic than a hydroxy radical, which has been considered as the main cause of oxidative stress.

Thus, attention has been paid in recent years particularly to (i) detection of acrolein that is generated in a cell and (ii) elucidation of a relationship between an oxidative stress-related disease and acrolein.

For example, Non-patent Literature 1 discloses a novel compound that selectively reacts particularly with acrolein among molecules that are present in a living organism.

CITATION LIST

Non-Patent Literature

Non-Patent Literature 1

ACS Sens. 2016, 1, 623-632.

SUMMARY OF INVENTION

Technical Problem

A compound disclosed in Non-patent Literature 1 (Compound 4 of FIG. 5, hereinafter referred to as "TAMRA-PhN$_3$") has an excellent property of rapidly reacting with acrolein under mild conditions, and can be sufficiently used to, for example, detect acrolein.

However, TAMRA-PhN$_3$ has room for further improvement in reactivity with acrolein in order to achieve, for example, (i) detection of a smaller amount of acrolein and (ii) a more rapid reaction with acrolein.

The present invention has been made in view of the above problems, and an object of the present invention is to provide, for example, (i) a novel, highly reactive drug that reacts with acrolein and (ii) a use thereof.

Solution to Problem

In order to attain the object, the present invention includes aspects described below.

1) A drug that reacts with acrolein, the drug containing:
a compound having a chemical structure represented by Formula (1):

wherein
R1 and R2 each independently represent a hydrogen atom, a halogen atom, or an alkyl group that has 1 to 5 carbon atoms and that may be substituted by at least one halogen atom, provided that at least one of R1 and R2 is the alkyl group having 1 to 5 carbon atoms;
R3, R4, and R each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms (provided that a hydrogen atom constituting the alkyl group may have a substituent selected from a halogen atom, a hydroxy group, and an amino group that may have a substituent);
n is an integer of not less than 1 and not more than 5; and
✻ is a binding site to another chemical structure.

2) A compound represented by Formula (10):

wherein
R1 and R2 each independently represent a hydrogen atom, a halogen atom, or an alkyl group that has 1 to 5 carbon atoms and that may be substituted by at least one halogen atom, provided that at least one of R1 and R2 is the alkyl group having 1 to 5 carbon atoms;
R3, R4, and R each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms (provided that a hydrogen atom constituting the alkyl group may have a substituent selected from a halogen atom, a hydroxy group, and an amino group that may have a substituent);
n is an integer of not less than 1 and not more than 5; and
a rhodamine-based coloring reagent is bound at ✻.

Advantageous Effects of Invention

An aspect of the present invention makes it possible to provide, for example, (i) a novel, highly reactive drug that reacts with acrolein and (ii) a use thereof.

DESCRIPTION OF EMBODIMENTS

[1. Drug that Reacts with Acrolein]

A drug that reacts with acrolein (hereinafter may also be referred to as a "reactive drug") in accordance with an embodiment of the present invention contains, as a compound that reacts with acrolein, a compound having a chemical structure represented by Formula (1). This compound may be a compound represented by Formula (10) and described in the section [2. Novel compound]. The reactive drug may substantially contain only the compound having the chemical structure represented by Formula (1). Alternatively, the reactive drug may be a composition containing (i) the compound having the chemical structure represented by Formula (1) and (ii) a substance other than the compound (i).

(1)

Acrolein (CH$_2$=CHCHO) is more generated in a cell loaded with oxidative stress, such as a cancer cell than in a normal cell (e.g., an allogeneic cell loaded with no oxidative stress). A triazoline reactant is produced by reaction between an azide group (N$_3$ group) in Formula (1) and acrolein. Detection of the triazoline reactant makes it possible to detect acrolein. The reactive drug in accordance with an embodiment of the present invention is highly reactive to acrolein. This makes it possible to achieve, for example, (i) detection of a smaller amount of acrolein and (ii) a more rapid reaction with acrolein.

Note that the expression of "the reactive drug is highly reactive to acrolein" means, for example, that the reactive drug is more highly reactive to acrolein than a compound in which R1 and R2 in Formula (1) are both hydrogen atoms (e.g., TAMRA-PhN$_3$ disclosed in Non-patent Literature 1). Reactivity to acrolein can be evaluated in accordance with, for example, an amount of the triazoline reactant produced per unit time. Alternatively, assuming that a degree of intracellular accumulation of the triazoline reactant is regarded as the amount of the triazoline reactant produced per unit time, it is possible to evaluate reactivity to acrolein in accordance with a rapid intracellular accumulation property of the triazoline reactant (see also Examples).

(R1 and R2)

In Formula (1), R1 and R2 each independently represent a hydrogen atom, a halogen atom, or an alkyl group that has 1 to 5 carbon atoms and that may be substituted by at least one halogen atom. Note, however, that at least one of R1 and R2 is the alkyl group having 1 to 5 carbon atoms.

Examples of the halogen atom include a fluorine atom, a chlorine atom, a bromine atom, an iodine atom, and an astatine atom. Note that the fluorine atom and the astatine atom may be isotopes.

The alkyl group having 1 to 5 carbon atoms may be either linear or branched. The alkyl group has a hydrogen atom that may be substituted or unsubstituted by the at least one halogen atom. Examples of the alkyl group that has 1 to 5 carbon atoms and that has an unsubstituted hydrogen atom include a methyl group, an ethyl group, a propyl group, an isopropyl group, an n-butyl group, an isobutyl group, a tert-butyl group, an n-pentyl group, an isopentyl group, a tert-pentyl group, and a sec-pentyl group.

R1 and R2 may be identical to or different from each other. In order to achieve a higher reactivity with acrolein, R1 and R2 may each be preferably an alkyl group that has 1 to 5 carbon atoms and that is substituted or unsubstituted by the at least one halogen atom, and may be more preferably alkyl groups that are identical to each other. Note that preferably 1 to 4 carbon atoms, and more preferably 2, 3, or 4 carbon atoms may constitute the alkyl group.

In another aspect, it may be preferable that one of R1 and R2 be the alkyl group that has 1 to 5 carbon atoms and that is substituted or unsubstituted by the at least one halogen atom and that the other one of R1 and R2 be the halogen atom (in particular, a fluorine or astatine isotope). Note that preferably 1 to 4 carbon atoms, and more preferably 2, 3, or 4 carbon atoms may constitute the alkyl group.

(R3, R4, and R)

In Formula (1), R3, R4, and R each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms. Note, however, that a hydrogen atom constituting the alkyl group may be substituted by a substituent selected from a halogen atom, a hydroxy group, and an amino group that may have a substituent.

The definition and exemplary description of the halogen atom is similar to that described in R1 and R2.

Examples of the amino group that may have a substituent include an unsubstituted amino group, an alkylamino group, a (hetero)aryl amino group, and the like. For example, 1 to 5 carbon atoms constitute each alkyl group included in the alkylamino group. The (hetero)aryl amino group refers to a group in which at least one hydrogen atom constituting the amino group is substituted by an aryl group (i.e., an aryl group or a heteroaryl group) that may have a hetero atom. Examples of each (hetero)aryl group included in the (hetero)aryl amino group include, for example, a (hetero)aryl group in which 3 to 20 (preferably 4 to 12) atoms form a framework of a ring structure. Note that examples of the hetero atom included in the heteroaryl group include a sulfur atom, a nitrogen atom, and an oxygen atom.

Examples of the alkoxy group having 1 to 5 carbon atoms include a methoxy group, an ethoxy group, a propoxy group, an isopropoxy group, and a butoxy group.

Examples of the alkylthio group having 1 to 5 carbon atoms include a methylthio group, an ethylthio group, a propylthio group, a butylthio group, and a pentylthio group.

The definition and exemplary description of the alkyl group that has 1 to 5 carbon atoms and that has an unsubstituted hydrogen atom is similar to that described in R1 and R2. Note that preferably 1 to 4 carbon atoms, and more preferably 1 to 3 carbon atoms may constitute the alkyl group. Note, however, that at least one of hydrogen atoms constituting the alkyl group may be substituted by a substituent selected from a halogen atom, a hydroxy group, and an amino group that may have a substituent. Note here that examples of the halogen atom and of the amino group that may have a substituent include examples identical to those mentioned as R3, R4, and R.

R3 and R4 may be identical to or different from each other. Note, however, that R3 and R4 may be preferably identical to each other. Rs that bind to a single carbon atom may be identical to or different from each other. Note, however, that Rs may be preferably identical to each other.

R3, R4, and R may be preferably each independently a hydrogen atom, a halogen atom, or an alkyl group that has 1 to 5 carbon atoms and that may be substituted by at least one halogen atom. The definition and exemplary description of the alkyl group that has 1 to 5 carbon atoms and that may be substituted by at least one halogen atom is similar to that described in R1 and R2.

(n)

In Formula (1), n may be an integer of not less than 1 and not more than 5, but n may be preferably 1 or 2, and more preferably 1.

(Exemplary Description of Preferable Combination of R1, R2, R3, and R4 Located on Single Ring)

Exemplary description of combination <1>: In Formula (1), R1, R2, R3, and R4 each independently represent a hydrogen atom, a halogen atom, or an alkyl group that has 1 to 5 carbon atoms and that may be substituted by at least one halogen atom, provided that at least one of R1 and R2 is the alkyl group having 1 to 5 carbon atoms.

Exemplary description of combination <2>: In Formula (1), R3, and R4 each independently represent a hydrogen atom, a halogen atom, or an alkyl group that has 1 to 5 carbon atoms and that may be substituted by at least one halogen atom, and R1 and R2 are each the alkyl group having 1 to 5 carbon atoms.

Exemplary description of combination <3>: In Formula (1), R3 and R4 each independently represent a hydrogen atom, a halogen atom, or an alkyl group that has 1 to 5 carbon atoms and that may be substituted by at least one halogen atom, and one of R1 and R2 is the alkyl group having 1 to 5 carbon atoms, and the other one of R1 and R2 is a halogen atom.

Exemplary description of combination <4>: In Exemplary description of combination <1> or <2> above, R3 and R4 are each independently the hydrogen atom or the halogen atom, and R1 and R2 are each the alkyl group having 1 to 5 carbon atoms.

Exemplary description of combination <5>: In Exemplary description of combination <3> above, R3 and R4 are each independently the hydrogen atom or the halogen atom.

(※)

In Formula (1), ※ is a binding site to another chemical structure as described earlier. Examples of the another the chemical structure include labelled compounds such as a coloring reagent and a marker. Such a labelled compound may be bound to ※ via a linker as necessary. To ※, preferably a coloring reagent, more preferably a rhodamine-based coloring reagent, and still more preferably 5-carboxytetramethylrhodamine or 6-carboxymethyltetramethyl-rhodamine, or a derivative thereof is bound.

(Rhodamine-Based Coloring Reagent)

A rhodamine-based coloring reagent is a generic name for a coloring reagent having a basic framework of rhodamine. Examples of the rhodamine-based coloring reagent include a coloring reagent whose basic framework is shown by Formula (2) below.

(2)

In Formula (2), R10, R11, R12, and R13 each independently represent a hydrogen atom or an alkyl group having 1 to 5 carbon atoms. The definition and exemplary description of the alkyl group having 1 to 5 carbon atoms is similar to that described in R1 and R2 in Formula (1). Note that preferably 1 to 4 carbon atoms, and more preferably 1 to 3 carbon atoms may constitute the alkyl group. In a case where R10 and R11 are alkyl groups, these alkyl groups may form a ring structure by binding to each other. In a case where R12 and R13 are alkyl groups, these alkyl groups may form a ring structure by binding to each other. Alternatively, in a case where at least one of R10 and R11 is an alkyl group, the alkyl group may form a ring structure by binding to a carbon atom that is adjacent to a carbon atom to which —NR10R11 binds (a carbon atom that is adjacent on an aryl ring to a carbon atom to which NR10R11 binds). Further alternatively, in a case where at least one of R12 and R13 is an alkyl group, the alkyl group may form a ring structure by binding to a carbon atom that is adjacent to a carbon atom to which —NR12R13 binds (a carbon atom that is adjacent on an aryl ring to a carbon atom to which —NR12R13 binds).

In Formula (2), R10, R11, R12, and R13 may be groups that are identical to each other. For example, R10, R11, R12, and R13 may all be hydrogen atoms, or may all be identical alkyl groups each having 1 to 5 carbon atoms.

In Formula (2), -※ indicates binding to another chemical structure. For example, -※ is binding to ※ in Formula (1).

Note that, in Formula (2), a hydrogen atom may be substituted or unsubstituted by any of substituents such as a halogen atom, a hydroxy group, and an alkyl group having 1 to 5 carbon atoms. The definition and exemplary description of the halogen atom and the alkyl group having 1 to 5 carbon atoms is similar to that described in R1 and R2 in Formula (1).

(Isotope-Containing Compound)

In the compound having the chemical structure represented by Formula (1), as described earlier, in a case where R1, R2, R3, R4, and R each contain a halogen atom, and/or in a case where R10, R11, R12, and R13 in Formula (2) each contain a halogen atom, at least one of these halogen atoms may be a fluorine isotope ($^{18}F$ etc.) or an astatine isotope ($^{210}At$, $^{211}At$, etc.). Furthermore, at least one of carbon atoms possessed by the compound (preferably carbon atoms possessed by any of R1, R2, R3, R4, R, R10, R11, R12, and R13) may be a carbon isotope ($^{14}C$ etc.).

(Other Component(s) that May be Contained in Reactive Drug, Etc.)

The reactive drug in accordance with an embodiment of the present invention may further contain, as necessary, a liquid (solvent or dispersion medium) that dissolves or disperses the compound having the chemical structure represented by Formula (1); a stabilizing agent and other additive(s); and the like.

Note that the reactive drug may be stored in a container as necessary. The reactive drug may be further provided together with an instruction manual in which such applications and instructions for use as described in the section [4. Application of drug that reacts with acrolein] are recorded.

[2. Novel Compound]

A novel compound in accordance with an embodiment of the present invention is a compound represented by Formula (10) below.

The definition and exemplary description of R1, R2, R3, R4, R, and n in Formula (10) is similar to the definition of Formula (1).

To ※, the rhodamine-based coloring reagent described earlier is bound. Specifically, the novel compound in accordance with an embodiment of the present invention is the compound that has the chemical structure represented by Formula (1) and in which ※ is the rhodamine-based coloring reagent. From the viewpoint of affinity with a biological sample including, for example, a cell, the rhodamine-based coloring reagent is particularly preferably 5-carboxytetramethylrhodamine or 6-carboxymethyltetramethylrhodamine, or a derivative thereof.

(Isotope-Containing Compound)

As in the case of the compound having the chemical structure represented by Formula (1), in a case where R1, R2, R3, R4, and R each contain a halogen atom, and/or in a case where R10, R11, R12, and R13 in Formula (2) each contain a halogen atom, at least one of these halogen atoms may be a fluorine isotope ($^{18}F$ etc.) or an astatine isotope ($^{210}At$, $^{211}At$, etc.). Furthermore, at least one of carbon atoms possessed by the compound (preferably carbon atoms possessed by any of R1, R2, R3, R4, R, R10, R11, R12, and R13) may be a carbon isotope ($^{14}C$ etc.).

(Exemplary Description of More Specific Compound)

Examples of a compound represented by Formula (10) include the following 5-carboxymethylrhodamine-diisopropylphenylazide and 6-carboxymethylrhodamine-diisopropylphenylazide (collectively called TAMRA-diisopropylphenylazide, and 5-carboxymethylrhodamine-diisopropylphenylazide only is represented by the chemical formula below).

(Application of Compound)

The novel compound in accordance with an embodiment of the present invention can be used as, for example, a compound that reacts with acrolein and that has been described in the section [1. Drug that reacts with acrolein]. The novel compound is excellent in affinity with a biological sample including, for example, a cell, and a triazoline reactant produced by reaction with acrolein rapidly accumulates in a cell and stains the cell. This results in achievement of, for example, selective and highly sensitive detection of a cell that produces more acrolein than a normal cell (see also Examples).

[3. Method for Producing Compound]

(Method for Producing Compound)

The compound represented by Formula (10) can be produced by, for example, the following method.

In a first stage, a compound represented by Formula (C) is obtained by reacting, in the presence of an appropriate solvent, (i) a compound represented by Formula (A) and (ii) a compound represented by Formula (B). A reaction carried out in the first stage is specifically a reaction in which an amido bond is formed between (a) an activated carboxy group (NHS form) possessed by the compound represented by Formula (B) and (b) an alkylamino group possessed by the compound represented by Formula (A). Examples of the solvent used in the first stage include aprotic polar solvents such as dimethylformamide (DMF) and dimethyl sulfoxide (DMSO).

Next, in a second stage, the compound represented by Formula (10) is obtained by converting an amino group possessed by the compound represented by Formula (C) to an azide group in the presence of an appropriate solvent. A reaction carried out in the second stage is specifically a reaction in which an amino group possessed by primary amine is diazotized by action thereon of nitrous acid, nitrite, or the like, and the amino group thus diazotized is converted to an azide group by further action thereon of sodium azide or the like. Examples of the solvent used in the first stage include aqueous acidic solvents such as an aqueous acetic acid solution and an aqueous hydrochloric acid solution.

For the method for producing the compound, it is also possible to see the descriptions of Examples and the descriptions of ACS Sens. 2016, 1, 623-632. (Non-patent Literature 1). Furthermore, the compound having the chemical structure represented by Formula (1) can also be produced with reference to these descriptions.

[4. Application of Drug that Reacts with Acrolein]

The reactive drug in accordance with an embodiment of the present invention is highly reactive to acrolein. Thus, the reactive drug can be suitably used in, for example, the applications below. Note that, when used in any of the applications, the reactive drug in accordance with an embodiment of the present invention is subjected to a contact step of bringing the reactive drug into contact with an object that may contain acrolein (a reaction step of reacting acrolein and the compound having the chemical structure represented by Formula (1)). Furthermore, a reaction method in accordance with an embodiment of the present invention brings a detection target (test sample) into contact with the reactive drug in accordance with an embodiment of the present invention.

(1) Application to Detection of Acrolein

A method for detecting acrolein in accordance with an embodiment of the present invention includes: a contact step of contacting a detection target (test sample) with the reactive drug in accordance with an embodiment of the present invention; and a detection step of detecting a reaction product of acrolein and the compound having the chemical structure represented by Formula (1).

The contact step can be carried out in, for example, a solvent that dissolves the compound having the chemical structure represented by Formula (1). The compound has a concentration that is not particularly limited provided that acrolein can be detected. Note, however, that the concentration of the compound has a lower limit that is, for example, not less than 0.1 μM, and may be preferably not less than 0.5 μM. In order to prevent or reduce background noise, the concentration of the compound has an upper limit that is, for example, not more than 2 μM, and may be preferably not more than 1.5 μM, and more preferably not more than 1.1 μM. Note that a reaction between the compound and acrolein proceeds, for example, under normal temperature and normal pressure.

The detection target is not particularly limited provided that the detection target is an object that may contain acrolein. Examples of the detection target include biologically derived samples such as a living cell and a part of a tissue derived from a living organism. The compound having the chemical structure represented by Formula (1) selectively and rapidly reacts with acrolein among various products (including an oxidative stress product) produced by a cell loaded with oxidative stress.

The detecting step is carried out with use of, for example, another chemical structure that is possessed by the compound having the chemical structure represented by Formula (1) and that is bound to the binding site ※. For example, in a case where the another chemical structure is a labelled compound such as a coloring reagent or a marker, the labelled compound makes reacted acrolein visible. In the detection step, for example, it is detected whether the labelled compound is present, and/or the labelled compound is quantitatively detected. This makes it possible to determine whether the detection target contains acrolein. In a case where the detection target contains acrolein, it is possible to determine the amount (absolute amount or relative amount) of the acrolein.

Between the contact step and the detecting step, a washing step of washing the detection target may be carried out as necessary. By carrying out the washing step, it is possible to remove a substance that is contained in the compound having the chemical structure represented by Formula (1) and that has not reacted with acrolein (for example, in a case where the detection target is a sample including a cell, a substance that has reacted with acrolein accumulates in the cell).

(2) Application to Examination of Oxidative Stress, Application to Examination of Oxidative Stress-Related Disease The present applications are each a form of "(1) Application to detection of acrolein" (described earlier) in which the detection target is a biologically derived sample including a cell, such as a living cell or a living tissue. In diseases related to oxidative stress (oxidative stress-related diseases), such as cancer, Alzheimer's disease, and cerebral infarction, acrolein is more generated from a cell loaded with oxidative stress than from a normal cell. Furthermore, acrolein, which is an oxidative stress product, is more generated from a cell that has not reached a disease state but is loaded with oxidative stress, than from a normal cell. Then, a reaction product of (i) the compound having the chemical structure represented by Formula (1) and (ii) acrolein selectively accumulates in a cell in which much acrolein is generated.

In the present applications, in accordance with a detection result obtained in the detection step in "(1) Application to detection of acrolein" (described earlier), a simple test for the presence or absence of oxidative stress and/or a degree thereof is carried out, and/or a simple test for, for example, the presence or absence of the possibility of suffering from a oxidative stress-related disease is/are carried out. Results of these tests can also be used as a material for a physician to carry out a diagnosis.

(3) Application to Cellular Testing

The present application is a form of "(1) Application to detection of acrolein" (described earlier) in which the detection target is a living cell or a living tissue. Examples of the living tissue include a biopsy sample and a living tissue produced during a surgery (a tissue removed by the surgery or a tissue remaining on the living organism side). Particularly preferable examples of the living tissue include a cancer biopsy sample and a living tissue produced during a cancer surgery.

In the present application, in accordance with the detection result obtained in the detection step in "(1) Application to detection of acrolein" (described earlier), a simple test for the presence or absence and/or localization of a cell (e.g., a cell loaded with oxidative stress) in which more acrolein is generated than in a normal cell is carried out with high accuracy, and/or a simple test for morphology of a cell in which much acrolein is generated is/are carried out. Results of these tests can also be used as a material for a physician to carry out a diagnosis. For example, in the case of removal of a cancer tissue by a surgery, a removed tissue or a tissue remaining on the living organism side is subjected to observation of the presence or absence, localization, and morphology of a cancer cell every time the removal is carried out. A result obtained from the observation can be used to carry out, for example, histopathologic diagnosis and cyto-diagnosis (hereinafter abbreviated as "intraoperative diagnosis").

It is already reported that cancer is diagnosed by using a fluorescent probe to cause a cancer tissue to selectively emit light. For example, H. Ueo et al., Sci. Rep. 2015, 5, 12080 discloses a technique for identifying a cancer tissue or a normal tissue by spraying a specific fluorescent probe onto a specimen so as to cause a cancer tissue to selectively emit light in a few minutes. The specific fluorescent probe emits fluorescence by reaction with an enzyme that is highly expressed on a cancer cell membrane surface.

However, according to the above fluorescent probe, enzyme turnover amplifies fluorescence over time. This makes it difficult to observe cancer cell morphology. The incapability to observe the cancer cell morphology makes it difficult to apply the fluorescent probe to intraoperative diagnosis.

In contrast, use of the reactive drug in accordance with an embodiment of the present invention makes it possible to, for example, observe localization and morphology of a cancer cell in a living tissue in a short time. Thus, the reactive drug can also be applied to detection during intraoperative diagnosis that requires observation of a living tissue in a short time (see also Examples).

(4) Application to Delivery to Cell

A method of delivery to a cell in accordance with an embodiment of the present invention includes a contact step of bringing the reactive drug in accordance with an embodiment of the present invention into contact with a cell, which may be present in a tissue or in an individual. A reaction product of (i) the compound having the chemical structure represented by Formula (1) and (ii) acrolein selectively and rapidly accumulates in a cell in which acrolein is generated in vivo. This allows the compound having the chemical structure represented by Formula (1) to be selectively delivered to a cell in which much acrolein is generated. For example, the compound having the chemical structure represented by Formula (1) is a pharmaceutical drug (for example, the compound has an isotopic atom for use in medical treatment, or the another chemical structure that binds to ※ is a pharmaceutical drug).

Aspects of the present invention can also be expressed as below.

In summary, in order to attain the object, the present invention includes the following features.

1) A drug that reacts with acrolein, the drug containing:
a compound having a chemical structure represented by Formula (1):

$$\text{(1)}$$

wherein

R1 and R2 each independently represent a hydrogen atom, a halogen atom, or an alkyl group that has 1 to 5 carbon atoms and that may be substituted by at least one halogen atom, provided that at least one of R1 and R2 is the alkyl group having 1 to 5 carbon atoms;

R3, R4, and R each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms (provided that a hydrogen atom constituting the alkyl group may have a substituent selected from a halogen atom, a hydroxy group, and an amino group that may have a substituent);

n is an integer of not less than 1 and not more than 5; and

※ is a binding site to another chemical structure.

2) The drug recited in 1), wherein the drug is a composition containing the compound having the chemical structure represented by Formula (1).

3) The drug recited in 1) or 2), wherein R1 and R2 are each independently the alkyl group having 1 to 5 carbon atoms.

4) The drug recited in any one of 1) through 3), wherein R3, R4, and R are each independently the hydrogen atom or the alkyl group that has 1 to 5 carbon atoms and that may be substituted by at least one halogen atom.

5) The drug recited in any one of 1) through 4), wherein n is 1 or 2.

6) The drug recited in any one of 1) through 5), wherein a rhodamine-based coloring reagent is bound at ※.

7) The drug recited in 6), wherein the rhodamine-based coloring reagent is 5-carboxytetramethylrhodamine or 6-carboxytetramethylrhodamine, or a derivative thereof.

8) A compound represented by Formula (10):

$$\text{(10)}$$

wherein

R1 and R2 each independently represent a hydrogen atom, a halogen atom, or an alkyl group that has 1 to 5 carbon atoms and that may be substituted by at least one halogen atom, provided that at least one of R1 and R2 is the alkyl group having 1 to 5 carbon atoms;

R3, R4, and R each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms (provided that a hydrogen atom constituting the alkyl group may have a substituent selected from a halogen atom, a hydroxy group, and an amino group that may have a substituent);

n is an integer of not less than 1 and not more than 5; and a rhodamine-based coloring reagent is bound at ※.

9) A reaction method including: bringing acrolein into contact with a drug recited in any one of 1) through 7) or a compound recited in 8).

10) A method for detecting acrolein, including: a contact step of bringing, into contact with a drug recited in any one of 1) through 7) or a compound recited in 8), an object that may contain the acrolein; and a detection step of detecting a reaction product of the acrolein and a compound having a chemical structure represented by Formula (1) or a compound represented by Formula (10).

11) The method recited in 10), wherein the object that may contain the acrolein is a biologically derived sample including a cell.

The following description will more specifically discuss an embodiment of the present invention with reference to Examples. It is a matter of course that the present invention is not limited to the Examples below and that details of the present invention can have various aspects. Further, the present invention is not limited to the embodiments, but can be altered by a skilled person in the art within the scope of the claims. An embodiment derived from a proper combination of technical means disclosed in respective different embodiments is also encompassed in the technical scope of the present invention. Moreover, all the literatures described herein are thereby incorporated by reference.

EXAMPLES

[Example 1] Synthesis of TAMRA-Diisopropylphenylazide 5-carboxymethylrhodamine-diisopropylphenylazide (TAMRA-diisopropylphenylazide) synthesized in Example is a compound having a chemical structure represented by Formula (1), wherein R1 and R2 are each an isopropyl group, R3 and R4 are each a hydrogen atom, R is a hydrogen atom, and n is 1. TAMRA-diisopropylphenylazide is synthesized along a route as shown below.

To a diethyl ether solution (100 mL) of 2,6-diisopropylaniline (a compound 1) (20.9 g, 118 mmol), iodine (16.7 g, 130 mmol) and a saturated aqueous sodium bicarbonate solution (300 mL) were added at room temperature. Then, the resulting solution was stirred for 3 hours. A sodium thiosulfate pentahydrate was added to the resulting mixture so that an organic layer and an aqueous layer were separated.

Then, organic layers were extracted 3 times with use of diethyl ether. An organic layer obtained by combining the organic layers was washed with water and dried with anhydrous sodium sulfate. After filtration, the solution was distilled off under reduced pressure, and the resulting residue was purified with use of column chromatography (hexane), so that 2,6-diisopropyl-4-iodoaniline (a compound 2, 20 g) was obtained with a yield of 56%.

To a DMF solution (25 mL) of 2,6-diisopropyl-4-iodoaniline (the compound 2) (1.84 g, 6.07 mmol), copper (I) cyanide (0.67 g, 7.28 mmol) was added at room temperature. The resulting mixture was heated at 130° C. and stirred for 12 hours. Then, the mixture was allowed to cool down to room temperature, and water (125 mL) was added thereto. An organic matter was extracted with ethyl acetate. Then, the organic matter was washed with a saturated saline solution and dried with anhydrous sodium sulfate. After filtration, the solution was distilled off under reduced pressure, and the resulting residue was purified with use of column chromatography (hexane:ethyl acetate=25:1→10:1), so that 2,6-diisopropyl-4-cyanoaniline (a compound 3, 1.03 g) was obtained with a yield of 84%.

Under nitrogen atmosphere at 0° C., a reducing agent LiAlH4 (LAH, 137 mg, 3.53 mmol) was added to a THF solution (7 mL) of 2,6-diisopropyl-4-cyanoaniline (the compound 3) (143 mg, 0.71 mmol). The resulting mixture was stirred for 5 hours under heat reflux at 80° C. and then cooled to 0° C. Next, the reducing agent in excess was deactivated by dropping water (4 mL) and then dropping a 10% aqueous sodium hydroxide (4 mL) solution, and then was diluted with ethyl acetate (10 mL), subjected to Celite filtration, and washed with ethyl acetate. An organic layer was washed with water and then with a saturated saline solution, and dried with anhydrous sodium sulfate. After filtration, the solution was distilled off under reduced pressure, and the resulting residue was purified with use of column chromatography (hexane:ethyl acetate=10:1→5:1), so that 3,5-diisopropyl-4-aminobenzylamine (a compound 4, 144 mg) was obtained with a yield of 99%.

Under nitrogen atmosphere, 5-carboxymethylrhodamine-hydroxysuccinimide (TAMRA-OSu, a compound 5) (25.0 mg, 0.05 mmol) was added to a DMF solution (1 mL) of 3,5-diisopropyl-4-aminobenzylamine (the compound 4) (10.9 mg, 0.05 mmol) at room temperature. Then, the resulting solution was stirred for 12 hours. Thereafter, the solvent was distilled off under reduced pressure, so that a crude product (TAMRA-diisopropylphenylamine, a compound 6) was obtained in the form of an oily purple substance. The compound 6 was dissolved in acetic acid/water (1 mL/0.5 mL). To the resulting solution, sodium azide (8.8 mg, 0.13 mmol) and sodium nitrite (9.0 mg, 0.13 mmol) were added at 0° C. Then, the resulting solution was stirred for 1 hour. Thereafter, the solution was distilled off under reduced pressure, and the resulting residue was purified with use of an ultrafast preparative reversed-phase column (HPLC Cosmosil 5C18-AR-300, 20×250 mm, flow rate: 10 mL/min, detection: UV254 nm, mobile phase=0.1% TFA—water:0.1% TFA—acetonitrile=15:85→0:100), so that the title compound TAMRA-diisopropylphenylazide (a compound 7, 19.1 mg) was obtained with a yield of 56% (2 steps).

[Reference Example 1] Selective Detection of Acrolein

The following 11 cell lines were seeded in 96 wells ($4×10^4$ cells/well) and left to stand for 24 hours before treatment so that the cell lines were adhered to the wells.

Normal cell: normal human diploid fibroblast (TIG3), normal human umbilical vein endothelial cell (HUVEC), normal human mammary gland cell (MCF10A)

Cancer cell: SKBR3 (human breast cancer cell), MDA-MB-231 (human breast cancer cell), BxPC3 (human pancreatic cancer cell), HT29 (human colonic cancer cell), MCF7 (human breast cancer cell), A549 (human lung cancer cell), HeLaS3 (human cervical cancer cell), PC3 (human prostatic cancer cell)

Figure 1:
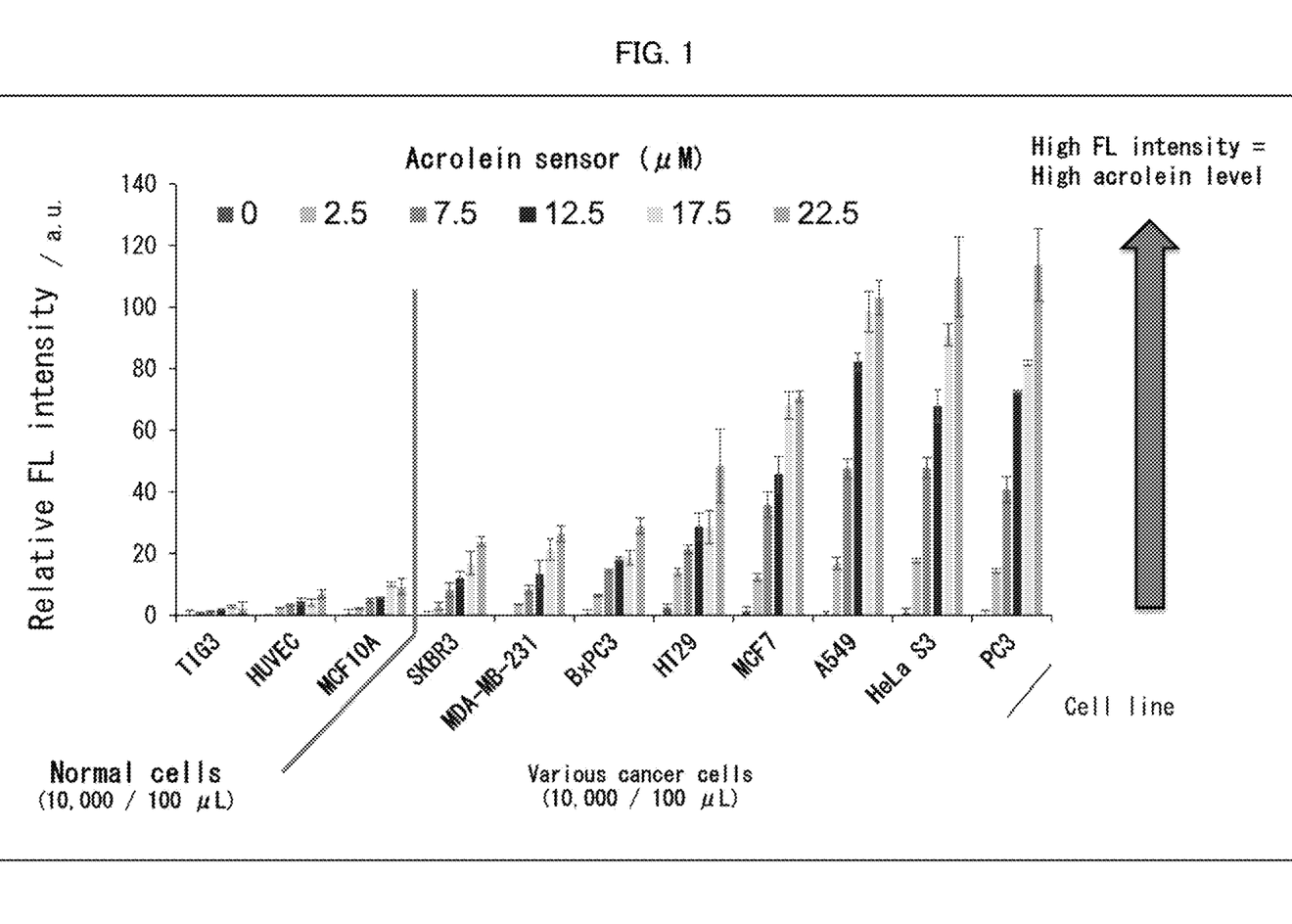
FIG. 1 shows a reference example and is a view illustrating a result of staining of a cancer cell line with use of TAMRA-PhN$_3$.

The cells were treated by adding, to media, 100 μL of TAMRA-PhN$_3$ solutions (2.5 μM, 7.5 μM, 12.5 μM, 17.5 μM, 22.5 μM) described in Non-patent Literature 1 and Example 2. Then, the cells were incubated at room temperature for 30 minutes. The cells were fixed by paraformaldehyde, and fluorescence was recorded with use of Spectra Max M2e (Molecular Devices, LLC.). FIG. 1 shows a result of measurement of fluorescence intensities.

In FIG. 1, the vertical axis represents a relative fluorescence intensity (arbitrary unit), and the horizontal axis represents a result of staining (fluorescence) of each normal or cancer cell. A higher fluorescence intensity shows a higher acrolein content. It was found that a higher concentration of TAMRA-PhN$_3$ results in an increase in reaction product (fluorescence intensity) obtained in the reaction of acrolein with TAMRA-PhN$_3$.

[Reference Example 2] Staining of Cancer Tissue

Figure 2:
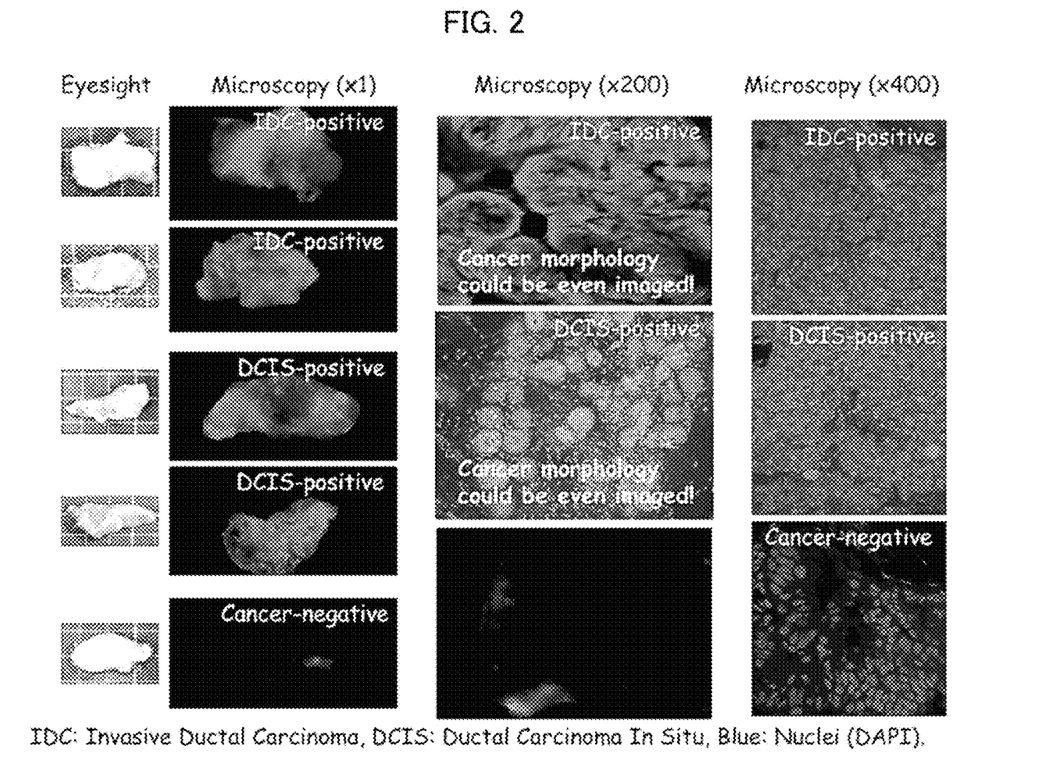
FIG. 2 shows a reference example and is a view illustrating a result of staining of a tissue with use of TAMRA-PhN$_3$.

An invasive ductal carcinoma-positive tissue (IDC-positive), a ductal carcinoma in situ-positive tissue (DCIS-positive), and a cancer-negative tissue (Cancer-negative) were each immersed in a TAMRA-PhN$_3$ solution (5 μM, 10 μM, 20 μM). These tissues were incubated at room temperature for 5 minutes. The tissues were each stained in a living tissue state. FIG. 2 shows a result of staining. Note that cell nuclei are stained with DAPI.

In FIG. 2, "Eyesight" indicates a photograph of each tissue that has been stained, and "Microscopy (×1)", "Microscopy (×200)", and "Microscopy (×400)" each indicate results of observations carried out with use of microscopes having respective magnifications of 1 time, 200 times, and 400 times.

As illustrated in FIG. 2, short-time incubation made it possible to directly identify a cancer cell that is in a living tissue state. It was found that use of TAMRA-PhN$_3$ makes it possible to observe localization and morphology of a cancer cell in detail in a living tissue.

Furthermore, given that short-time incubation made it possible to observe localization and morphology of a cancer cell, it has been suggested that TAMRA-PhN$_3$ is rapidly incorporated and accumulated in a cell. Among various stress products produced by a cell, only acrolein was successfully selectively imaged. Further studies have shown that TAMRA-PhN$_3$ is incorporated in a lysosome or an endoplasmic reticulum by an endocytic mechanism.

TAMRA-PhN$_3$ reacts with acrolein, and the resulting triazoline product is intracellularly converted to a highly reactive diazo compound, binds to a neighboring protein, and remains intracellularly and on the cell surface.

[Example 2] Sensitivity Comparison with Conventional Detection Reagent

Figure 3:
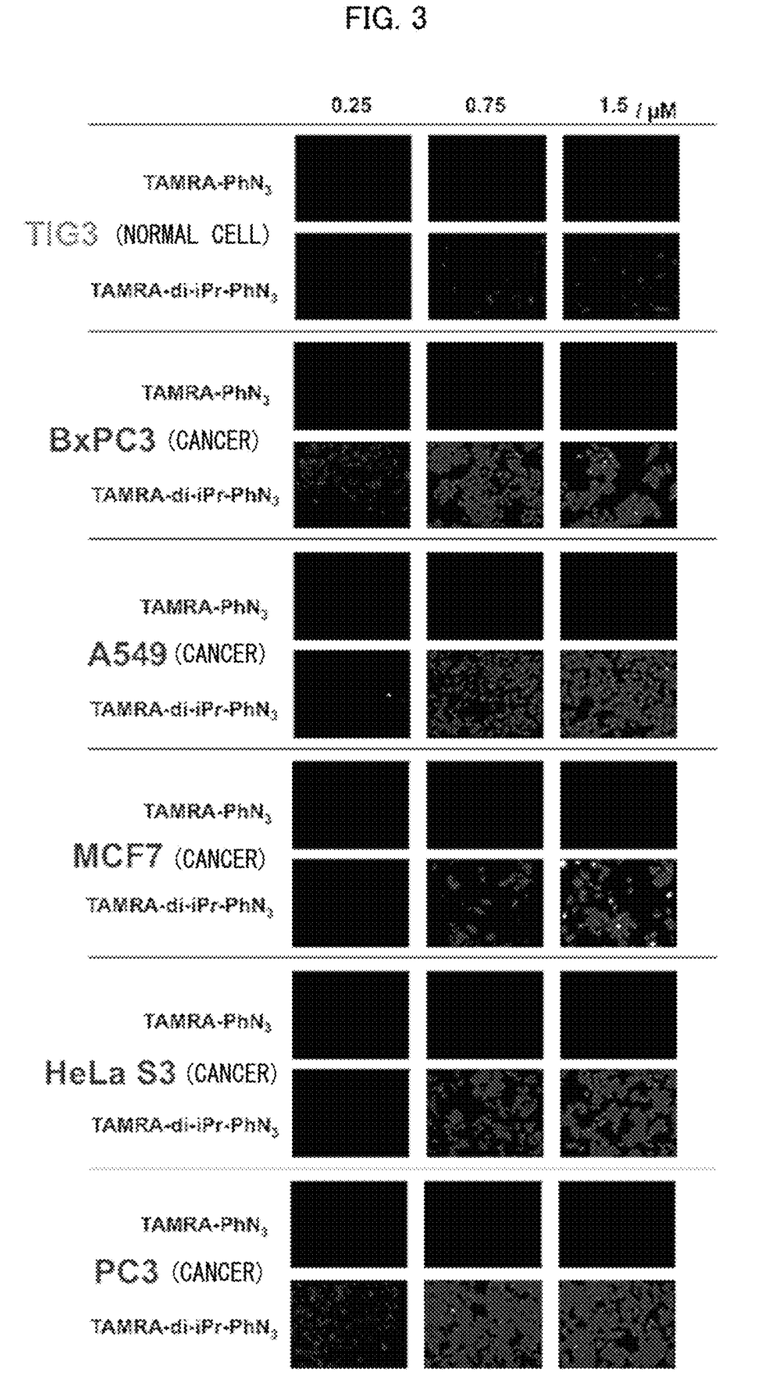
FIG. 3 is a view illustrating a result of staining of a normal cell and a cancer cell with use of (i) a reactive drug for use in detection of acrolein in accordance with an example of the present invention or (ii) TAMRA-PhN$_3$.

Respective detection sensitivities of a detection reagent (TAMRA-PhN$_3$) represented by Formula below and the compound 7 (TAMRA-di-iPr-PhN$_3$) prepared in Example 1 were compared. Cells illustrated in FIG. 3 (for description of cell strains, see also Reference Example 1) were each immersed in an aqueous solution, containing the detection reagent at a concentration of 0.25 μM, 0.75 μM, or 1.5 μM, for 5 minutes so as to be stained. FIG. 3 shows a result of staining.

As illustrated in FIG. 3, the compound 7 prepared in Example 1 was not less than 100 times more sensitive than TAMRA-PhN$_3$. Moreover, it was possible to identify localization and morphology of a cancer cell at a concentration at which localization and morphology of a cancer cell cannot be identified by TAMRA-PhN$_3$. For example, it has been suggested that TAMRA-di-iPr-PhN$_3$ is capable of detecting acrolein that has a concentration that is as low as pM level, whereas TAMRA-PhN$_3$ is capable of detecting acrolein that is generated from a cell and has an nM-level concentration.

CROSS REFERENCE TO RELATED APPLICATION

This application claims priority on Japanese Patent Application, Tokugan, No. 2018-129372 filed in Japan on Jul. 6, 2018, the entire contents of which are hereby incorporated by reference. The contents of all publications, including patent and patent application specifications cited in the present application, are also incorporated herein by reference in their entirety.

INDUSTRIAL APPLICABILITY

The present invention can be used as a drug for detection of oxidative stress diseases such as cancer and cerebral infarction, and can be used for, for example, life science research and medical treatment.

The invention claimed is:
1. A drug that reacts with acrolein, said drug comprising:
a compound having a chemical structure represented by Formula (1):

wherein
R1 and R2 each independently represent a hydrogen atom, a halogen atom, or an alkyl group that has 1 to 5 carbon atoms and that may be substituted by at least one halogen atom, provided that at least one of R1 and R2 is the alkyl group having 1 to 5 carbon atoms;
R3, R4, and R each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms provided that a hydrogen atom constituting the alkyl group may be substituted by a substituent selected from a halogen atom, a hydroxy group, and an amino group that may have a substituent;
n is an integer of not less than 1 and not more than 5; and
※ is a binding site to another chemical structure.
2. The drug as set forth in claim 1, wherein the drug is a composition containing the compound having the chemical structure represented by Formula (1).
3. The drug as set forth in claim 1, wherein R1 and R2 are each independently the alkyl group having 1 to 5 carbon atoms.
4. The drug as set forth in claim 1, wherein R3, R4, and R are each independently the hydrogen atom or the alkyl group that has 1 to 5 carbon atoms and that may be substituted by at least one halogen atom.
5. The drug as set forth in claim 1, wherein n is 1 or 2.
6. A compound represented by Formula (10):

wherein
R1 and R2 each independently represent a hydrogen atom, a halogen atom, or an alkyl group that has 1 to 5 carbon atoms and that may be substituted by at least one halogen atom, provided that at least one of R1 and R2 is the alkyl group having 1 to 5 carbon atoms;
R3, R4, and R each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms provided that a hydrogen atom constituting the alkyl group may be substituted by a substituent selected from a halogen atom, a hydroxy group, and an amino group that may have a substituent;
n is an integer of not less than 1 and not more than 5; and
a rhodamine-based coloring reagent is bound at ※.

7. A reaction method comprising:
bringing acrolein into contact with a drug recited in claim 1.

8. A method for detecting acrolein, comprising:
a contact step of bringing, into contact with a drug recited in claim 6, an object that may contain the acrolein; and
a detection step of detecting a reaction product of the acrolein and a compound having a chemical structure represented by Formula (1) or a compound represented by Formula (10).

9. The method as set forth in claim 8, wherein the object that may contain the acrolein is a biologically derived sample comprising a cell.

10. The compound as set forth in claim 6, wherein the rhodamine-based coloring reagent is 5-carboxytetramethylrhodamine or 6-carboxytetramethylrhodamine.

\* \* \* \* \*

UNITED STATES PATENT AND TRADEMARK OFFICE
CERTIFICATE OF CORRECTION

| | |
|---|---|
| PATENT NO. | : 12,122,918 B2 |
| APPLICATION NO. | : 17/256969 |
| DATED | : October 22, 2024 |
| INVENTOR(S) | : Katsunori Tanaka and Ambara Rachmat Pradipta |

It is certified that error appears in the above-identified patent and that said Letters Patent is hereby corrected as shown below:

On the Title Page

Item (57) ABSTRACT reads:
Provided are, for example, (i) a drug that reacts with acrolein and (ii) a use thereof. A drug that reacts with acrolein in accordance with an embodiment of the present invention contains a compound having a chemical structure represented by Formula (1):

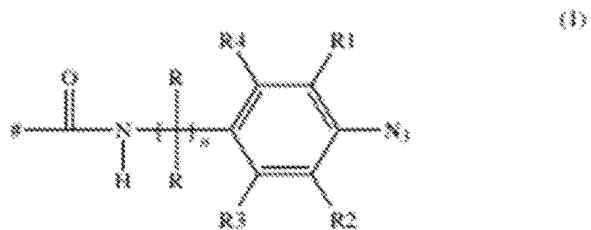

Whereas it should read:
Provided are, for example, (i) a drug that reacts with acrolein and (ii) a use thereof. A drug that reacts with acrolein in accordance with an embodiment of the present invention contains a compound having a chemical structure represented by Formula (1):

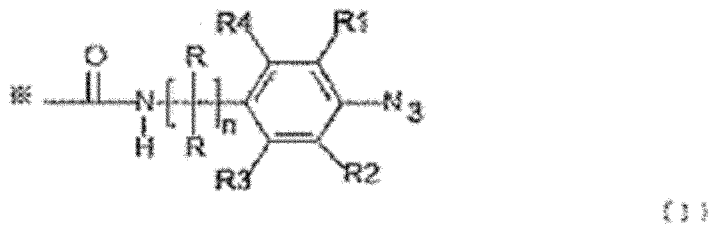

Signed and Sealed this
Twenty-fifth Day of February, 2025

Coke Morgan Stewart
*Acting Director of the United States Patent and Trademark Office*

CERTIFICATE OF CORRECTION (continued)
U.S. Pat. No. 12,122,918 B2

In the Claims

Column 18, Claim 1, Line 1 reads:

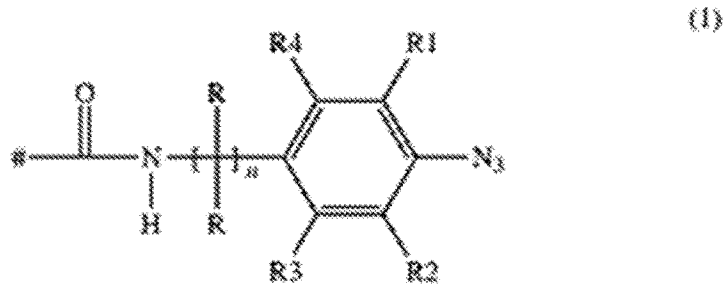

(I)

Whereas it should read:

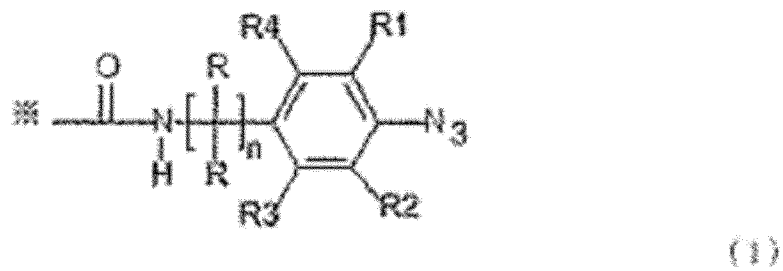

(I)

Column 18, Claim 6, Line 41 reads:

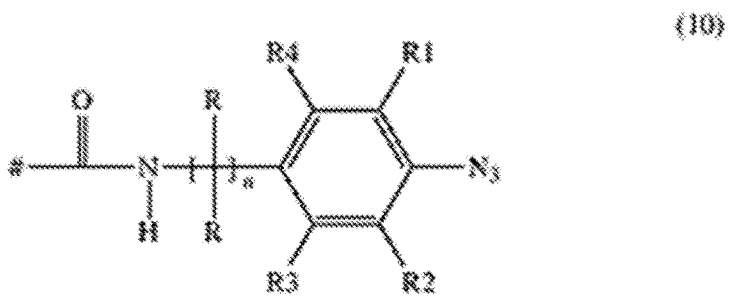

(I0)

Whereas it should read:

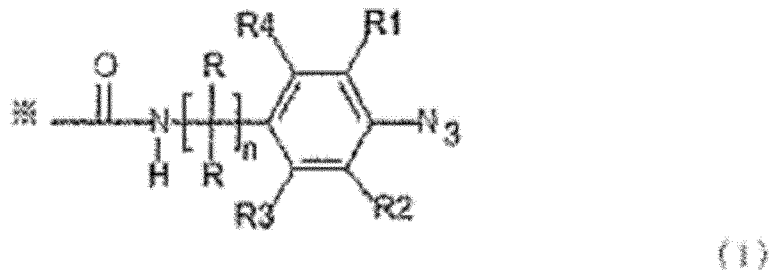

(I)